United States Patent [19]
Sheen et al.

[11] Patent Number: 5,665,907
[45] Date of Patent: Sep. 9, 1997

[54] ULTRASONIC IMAGING SYSTEM FOR IN-PROCESS FABRIC DEFECT DETECTION

[75] Inventors: Shuh-Haw Sheen; Hual-Te Chien, both of Naperville; William P. Lawrence; Apostolos C. Raptis, both of Downers Grove, all of Ill.

[73] Assignee: The University of Chicago, Chicago, Ill.

[21] Appl. No.: 609,955

[22] Filed: Mar. 4, 1996

Related U.S. Application Data

[63] Continuation-in-part of Ser. No. 301,120, Sep. 6, 1994, abandoned.

[51] Int. Cl.[6] .............................. G01L 5/04; G01N 29/00
[52] U.S. Cl. .............................. 73/159; 73/602; 73/598; 73/618
[58] Field of Search .............................. 73/159, 597, 599, 73/598, 600, 602, 618, 620, 627, 628, 629, 160

[56] References Cited

U.S. PATENT DOCUMENTS

| | | | |
|---|---|---|---|
| 5,271,284 | 12/1993 | Still et al. | 73/865.8 |
| 5,305,239 | 4/1994 | Kinra | 364/507 |
| 5,398,538 | 3/1995 | Williams et al. | 73/159 |
| 5,408,882 | 4/1995 | McKinley et al. | 73/597 |
| 5,438,872 | 8/1995 | Kobayashi et al. | 73/597 |
| 5,454,045 | 9/1995 | Perkins et al. | 382/181 |
| 5,471,878 | 12/1995 | Chiao et al. | 73/602 |
| 5,513,531 | 5/1996 | Sapia et al. | 73/602 |

*Primary Examiner*—Hezron E. Williams
*Assistant Examiner*—Richard A. Moller
*Attorney, Agent, or Firm*—Mason, Kolehmainen, Rathburn & Wyss

[57] ABSTRACT

An ultrasonic method and system are provided for monitoring a fabric to identify a defect. A plurality of ultrasonic transmitters generate ultrasonic waves relative to the fabric. An ultrasonic receiver means responsive to the generated ultrasonic waves from the transmitters receives ultrasonic waves coupled through the fabric and generates a signal. An integrated peak value of the generated signal is applied to a digital signal processor and is digitized. The digitized signal is processed to identify a defect in the fabric. The digitized signal processing includes a median value filtering step to filter out high frequency noise. Then a mean value and standard deviation of the median value filtered signal is calculated. The calculated mean value and standard deviation are compared with predetermined threshold values to identify a defect in the fabric.

10 Claims, 7 Drawing Sheets

ULTRASONIC IMAGING SYSTEM FOR IN-PROCESS FABRIC DEFECT DETECTION

BACKGROUND OF THE INVENTION

This is a continuation-in-part of prior application Ser. No. 08/301,120, filed Sep. 6, 1994 now abandoned.

CONTRACTUAL ORIGIN OF THE INVENTION

The United States Government has rights in this invention pursuant to Contract No. W-31-109-ENG-38 between the United States Government and Argonne National Laboratory.

1. Field of the Invention

The present invention relates to a method and system for monitoring textile characteristics, and more particularly to ultrasonic transducer apparatus, method and system for monitoring textile characteristics to detect fabric defects and anomalies.

2. Description of the Prior Art

Typically manual inspection is required to identify defects in fabrics during the manufacture and processing of the fabrics. Manual inspection arrangements are prone to human error and are time-consuming and inherently inefficient. A need exists for an automated system for detecting defects of the fabrics that is reliable and efficient.

Ultrasonic type testing systems for inspecting materials are known. For example, U.S. Pat. No. 4,368,438 issued Jan. 11, 1983 to Stienstra discloses an ultrasonic system for detecting and distinguishing between superimposed and single sheet-like objects moving along a transport path. The disclosed circuit includes an ultrasonic signal source, an ultrasonic signal receiver arranged at opposite sides of the transport path, an oscillator, an amplitude detector connected with the receiver and a phase detector. The amplitude detector is used to detect when a change occurs from a condition in which a sheet-like object is present to a condition in which no sheet-like object is present.

U.S. Pat. No. 3,780,570 issued Dec. 25, 1973 to Collins discloses an ultrasonic inspection device for nondestructively testing flat, bonded panels such as plywood or particle board panels. A plurality of roller type ultrasonic transducers are described as positioned on one side of a workpiece transporting line, while receiving transducers are placed on the other side of the line. Transmitters supply an ultrasonic pulse signal to each transmitting transducer. In the disclosed arrangement, a panel that is well bonded is identified by the associated receiving transducer receiving the ultrasonic signal.

It is an object of the present invention to provide an improved method, apparatus and system for monitoring textile characteristics to detect fabric defects and anomalies.

It is another object of the present invention to provide an improved method and system for monitoring textile characteristics using ultrasonic transducer apparatus to provide improved defect detection efficiency and reliable operation.

It is another object of the present invention to provide an improved method and system for monitoring textile characteristics using ultrasonic transducer apparatus to provide both internal and surface defect detection.

It is another object of the present invention to provide an improved method and system for monitoring textile characteristics using ultrasonic transducer apparatus to provide fabric defect detection and automatic defect characterization.

It is another object of the present invention to provide an improved method and system for monitoring textile characteristics overcoming some of the disadvantages of known arrangements for fabric defect detection.

SUMMARY OF THE INVENTION

In brief, these and other objects and advantages of the invention are provided by an ultrasonic transducer apparatus, method and system for monitoring textile characteristics. A plurality of ultrasonic transmitters generate ultrasonic waves relative to the fabric. An ultrasonic receiver means responsive to the generated ultrasonic waves from the transmitters receives ultrasonic waves coupled through the fabric and generates a signal. An integrated peak value of the generated signal is applied to a digital signal processor and is digitized. The digitized signal is processed to identify a defect in the fabric. The digitized signal processing includes a median value filtering step to filter out high frequency noise. Then a mean value and standard deviation of the median value filtered signal is calculated. The calculated mean value and standard deviation are compared with predetermined threshold values to identify a defect in the fabric.

BRIEF DESCRIPTION OF THE DRAWING

These and other objects and advantages of the present invention will become readily apparent upon consideration of the following detailed description and attached drawing, wherein.

DETAILED DESCRIPTION OF THE PREFERRED EMBODIMENT

Figure 1:
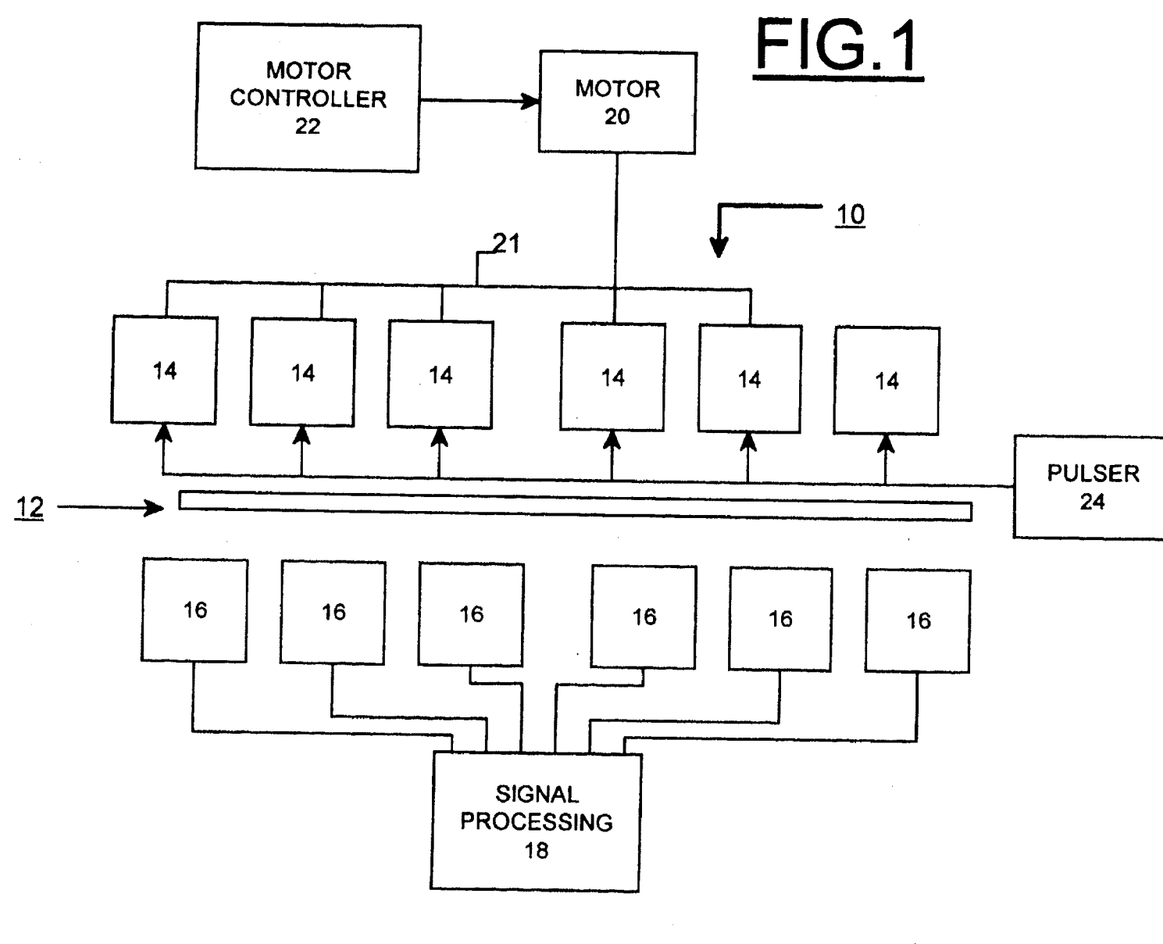
FIG. 1 is a schematic and block diagram representation of a textile monitoring system of the invention.

Referring to FIG. 1 of the drawing, there is shown a schematic and block diagram representation of a textile monitoring system according to the invention generally designated by the reference numeral 10. Textile monitoring system 10 provides on-line and continuous monitoring of textile quality of a fabric 12 with particular emphasis on fabric defects and anomalies. Other important features of the textile monitoring system 10 include detecting both surface and internal defects of the fabrics. Textile monitoring system 10 provides non-contact monitoring with fast response. Textile monitoring system 10 is sensitive to fabric thickness and uniformity. Fabric defects are detected independently of fabric color. Textile monitoring system 10 is a simple, low cost arrangement. Textile monitoring system 10 can be used to detect and identify fabric defects in order to provide corrective action regarding fabric defects.

Textile monitoring system 10 is an ultrasonic imaging system including a plurality of air-coupled ultrasonic transmitters 14 and a plurality of air-coupled ultrasonic receivers 16 and signal processing circuitry generally designated by the reference numeral 18. Textile monitoring system 10 uses at least two sets of ultrasonic-wave transducers 14 and 16 positioned across the fabric 12 to be inspected. Ultrasonic waves are sent from one side of the fabric 12 to the other side and the changes of the sound waves are measured and related to fabric defects. A database is developed for the automated intelligent inspection of fabric defects.

Transmitters 14 and receivers 16 can transmit and receive longitudinal waves of frequency between 0.1 and 1.0 MHz through the air. Frequencies in the order of 500 KHz can be used in the textile monitoring system 10. One or more pairs of transmitters 14 and receivers 16 and preferably an array of such pairs are placed next to a fabric web to detect any defects. The arrays of transducers 14 and 16 are non-contact sensors and can be operated in an on-loom mode by which the fabric 12 is moving through the spacing between the arrays of transducer transmitters 14 and receivers 16. Alternatively as shown, a motor 20 can be coupled for movement of the transmitters 14 and receivers 16 via a transducer holder indicated by a line 21 is operatively controlled by a motor controller 22.

Figure 2A:
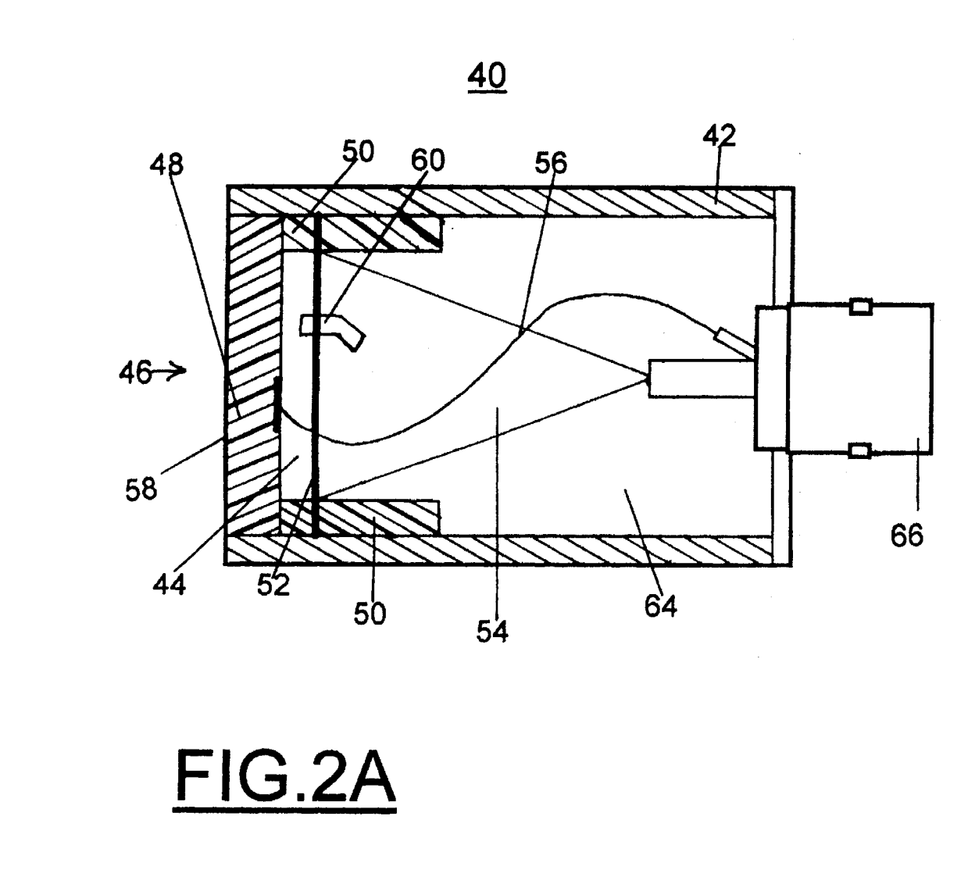
FIG. 2A is a partly schematic side view representation of an ultrasonic transducer apparatus of the textile monitoring system of FIG. 1.
Figure 2B:
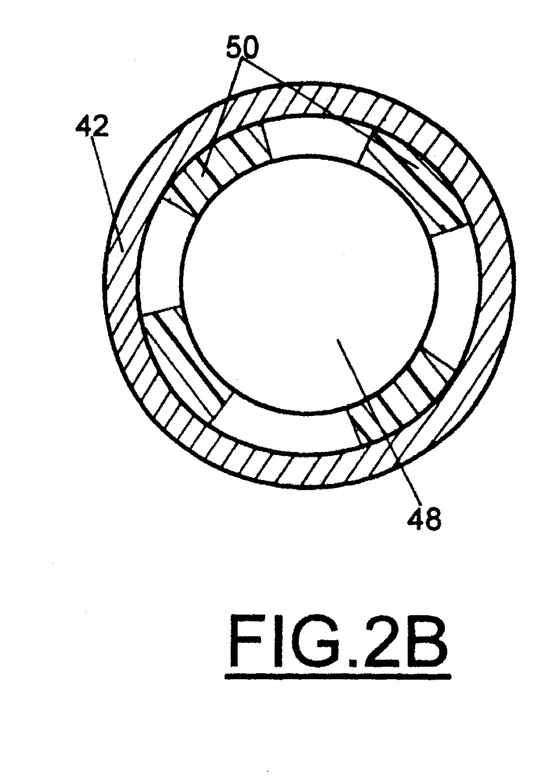
FIG. 2B is an end view of the ultrasonic transducer apparatus of FIG. 2A.

Transmitters 14 and receivers 16 advantageously are arranged as a linear transducer array including a selected number of sensing elements 14 and 16, depending on the width of the fabric under inspection. The basic design of each transmitters 14 and receivers 16 of the air-coupled transducer array is shown in FIGS. 2A and 2B. Alternatively, a stationary polyvinyl piezoelectric film can be used for the receivers 16, and focused transducers can be used for the transmitters 14.

A pulser 24 generates a pulse signal applied to the ultrasonic transmitters 14. Ultrasonic pulses generated by one array of transmitters 14 propagate through the fabric 12 and detected by the other array of receivers 16. Transmitters 14 are focused ultrasonic transducers.

Figure 1A:
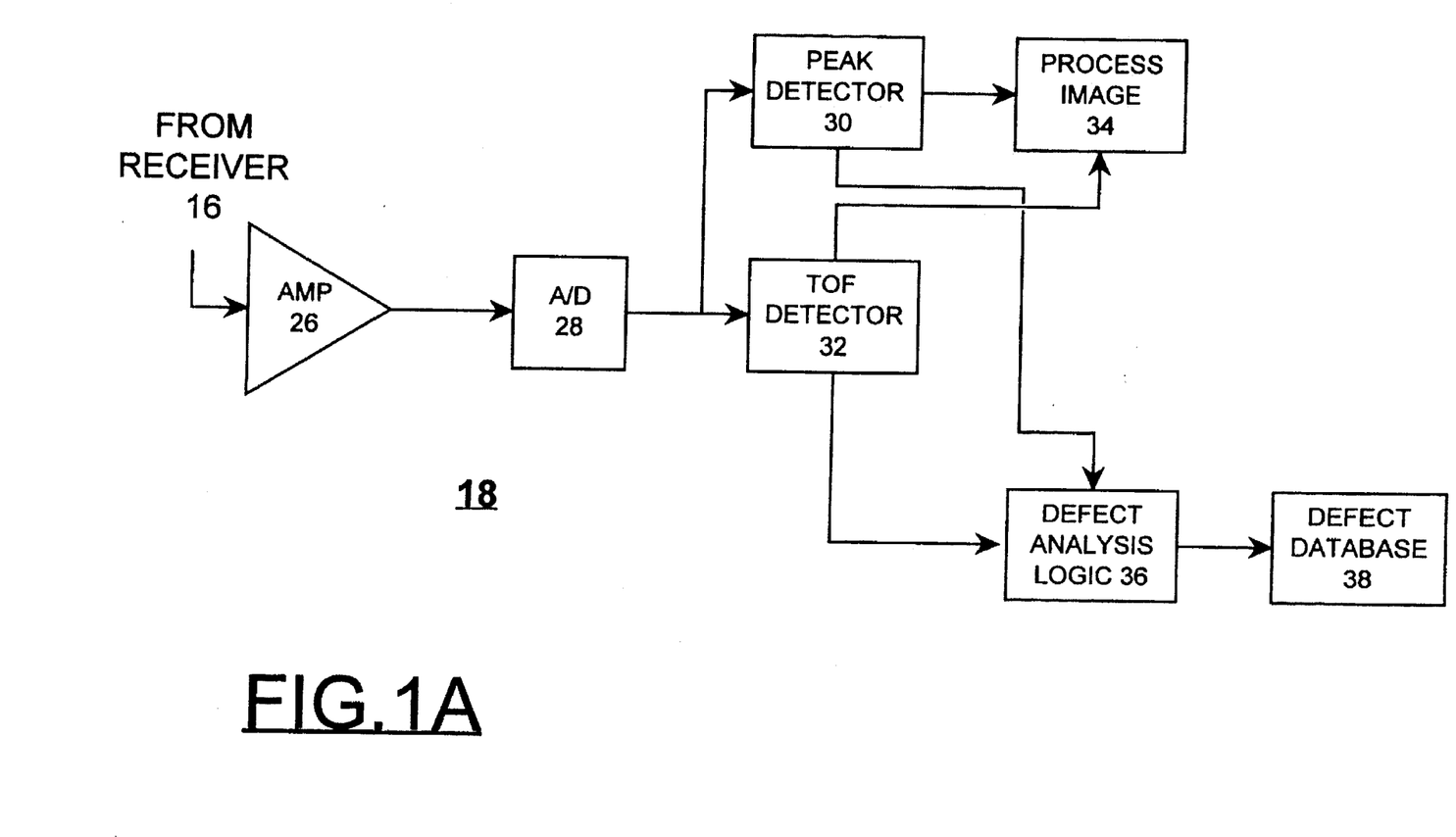
FIG. 1A is a schematic and block diagram representation of an improved signal processing circuitry of the textile monitoring system of FIG. 1.

Referring also to FIG. 1A, exemplary signal processing circuitry 18 is illustrated. Received signals from each receiver 16 is applied to a pre-amplifier 26 and amplified. The amplified signal is applied to an analog-to-digital (A/D) converter 28. Then peak amplitudes and times of flight are measured at a first block 30 labeled PEAK DETECTOR and a second block 32 labeled TOF DETECTOR, respectively. Two-dimensional images can be constructed from either the amplitude or the TOF variations at a block 34 labeled PROCESS IMAGE. Peak amplitude and time of flight values are converted to pixel intensity in the generated images. The received peak amplitude and time of flight signals are applied to a defect analysis logic block 36 and analyzed for their amplitudes and time-of-flights (TOF) to generate a signal that can be used to identify the defect and mark the fabric for corrective action. Defects identified at the defect analysis logic block 36 are stored in a database of defect values at a block 38 labeled DEFECT DATABASE.

Referring now to FIGS. 2A and 2B, there is shown an air-coupled transducer generally designated by the reference character 40 that advantageously can be used for the transmitters 14 and receivers 16. Air-coupled transducer 40 includes a housing 42, for example that is formed of steel, for containing a crystal 44 at a front-end section generally designated 46. Transducer 40 uses a specifically designated front-end section 46 having a special matching material 48 on the outer face of the crystal to improve impedance matching. The preferred matching material 48 is an air-filled epoxy to provide improved matching with the air. Smoother epoxy preferably is used for the receiver 16 as compared to the transmitter 14. Piezoelectric crystal 44 has a high acoustic impedance and is generally rigid to sound waves. Providing air bubbles within the epoxy matching material 48 lowers the acoustic impedance.

Use of a specially designed front-end matching material 48 containing air bubbles allows the transducer 40 to effectively transmit and receive longitudinal waves of frequency between 0.1 and 1.0 MHz through the air. A piezoelectric crystal can be used for crystal 44. A plurality of phenolic spacers 50 and an epoxy boundary 52 mount crystal 44 within the front-end section 46 of the housing 42. Crystal 44 is supported by a cone-shaped backing mass 54, for example that is formed of brass. A negative lead 56 is connected to a front surface 58 of the crystal 44. A positive lead 60 is connected to a rear surface 62 of the crystal 44. A lead-filled epoxy cavity filler 64 fills the cavity behind crystal 44 within the housing 42. A connector 66 mounted on the housing 42 is connected to the negative lead 58 and the positive lead 60 for coupling an electrical signal to or from the piezoelectric crystal 44.

Figure 3:
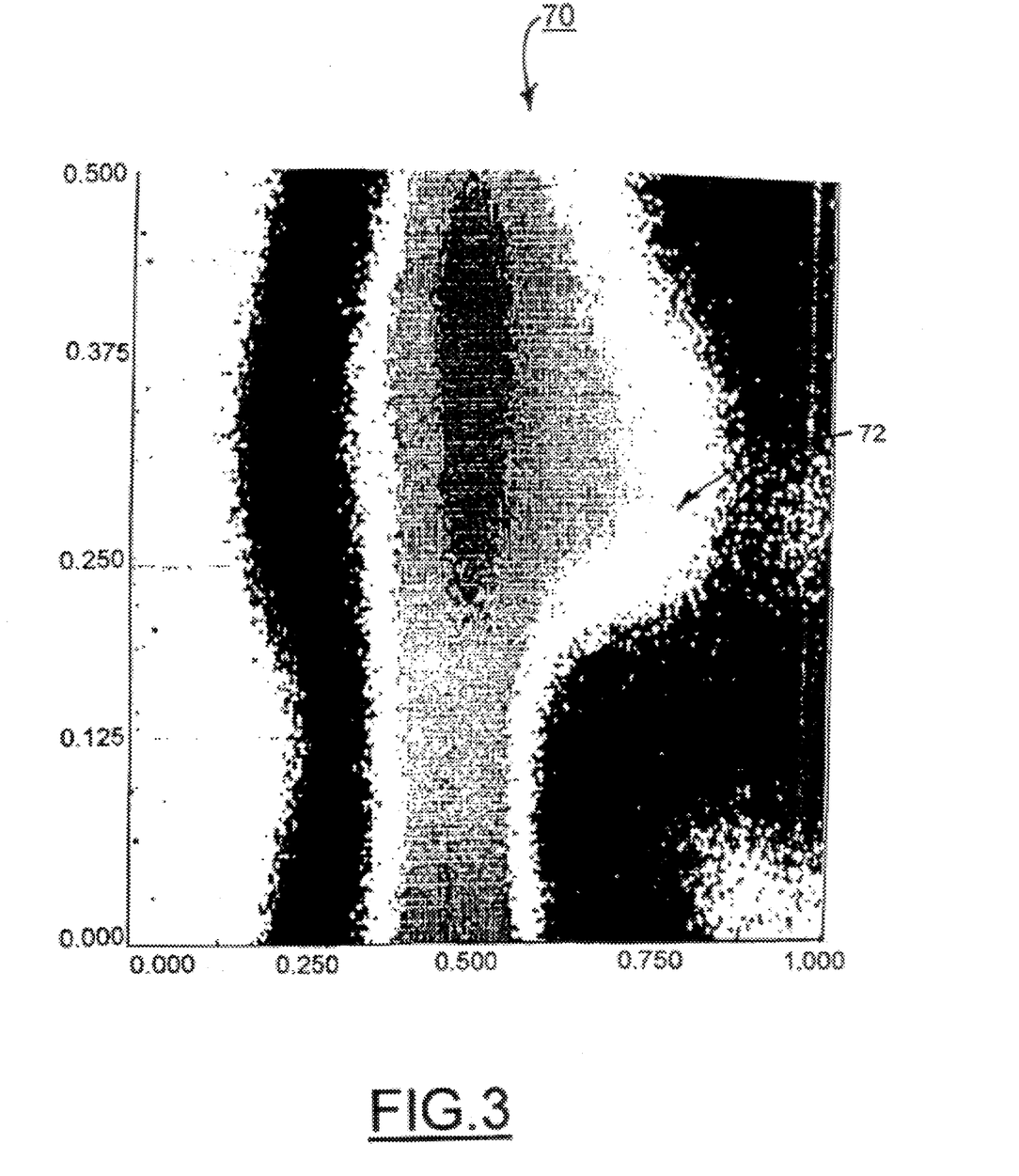
FIG. 3 is a graphical representation of an image including a defect generated by the system of FIG. 1.

FIG. 3 shows a two-dimensional ultrasonic through-transmission amplitude image 70 of a sample fabric 12 with missing fillings. Increased darkness in the image 70 corresponds to increased amplitude of a signal being processed. The image has a maximum vertical dimension of 0.5 and a maximum horizontal dimension of 1.0, for example 0.5"× 1.0". The central portion, of the image (approximately 0.25"×0.5") indicates the area including the defect as indicated by an arrow 72. Because fabric defects have many forms, such as missing filling, oily spots, and double picks, data base 38 and artificial intelligence logic 36 are also included in the textile monitoring system 10 for automatic defect characterization.

Figure 4:
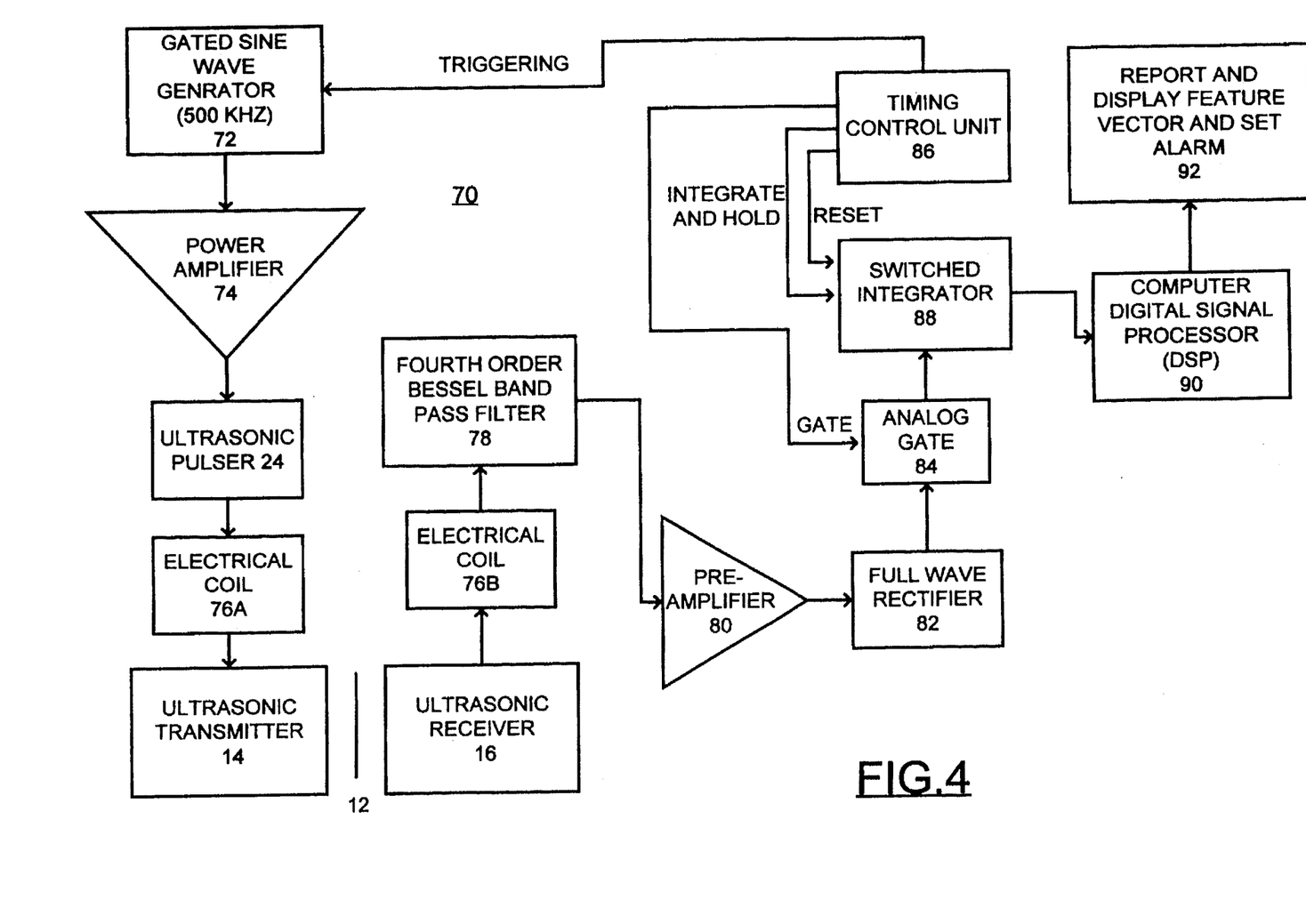
FIG. 4 is a schematic and block diagram representation of an improved signal processing circuitry of the textile monitoring system of FIG. 1.

Referring now to FIG. 4, there is shown an improved signal processing circuit 70. A gated sine wave generator 72 generates a sine wave signal having a frequency of approximately 500 KHZ when a triggering signal is applied to the generator 72. The generated sine wave signal is applied to a power amplifier 74 and is amplified. The amplified signal is applied to the ultrasonic pulser 24. An electrical coil 76A is coupled between the ultrasonic pulser 24 and the ultrasonic transmitter 14. The electrical coil 76A is used to provide better impedance match between the power supply 24 and the transducer 14.

In the preferred arrangement of the textile monitoring system 10, the transmitters 14 are implemented with 0.5 MHz, 1-inch OD, air-coupled, focused transducers that do not include a front-end matching material. Each ultrasonic transmitter 14 projects a beam size of approximately 0.2-inch on the fabric 12 which is roughly 1-inch away from the transmitter surface. The ultrasonic receivers 16 are air-coupled 0.5-inch OD flat-surface transducers.

It should be understood that the ultrasonic receivers 16 may be replaced by a simple reflection plate where in this configuration the transmitters 16 perform a dual role, sending out pulses and receiving echoes.

An electrical coil 76B is connected between the transducer 16 and a pre-amplifier 80 (which provides for example, 60 dB gain. The electrical coil 76B provides improved impedance matching, and thus enhances signal amplitude. A fourth order bessel band pass filter 78 band pass filters the signal from the ultrasonic receiver 16 and applies the filtered signal to the pre-amplifier 80. A variable inductor advantageously is used for both the electrical coils 76A and 76B for providing a selected matching inductance, for example, in a range between 20 microhenry and 100 microhenry.

Next full wave rectification of the amplified signal is provided by a full wave rectifier 82 connected to the output of the pre-amplifier 80. An analog gate 84 operatively controlled by a timing control unit 86 couples the full wave rectified signal to a switched integrator 88. The timing control unit 86 provides the triggering signal to the gated sine wave generator 72. The timing control unit 86 provides an integrate and hold signal and a reset signal to the switched integrator 88. The integrated peak value of the processed ultrasonic receiver signal is applied to a computer or digital signal processor (DSP) 90 which performs digitization of the integrated peak value signal and defect detection. DSP 90 generates a defect report and display feature vector and set alarm block 92. It should be understood that the defect detection and categorization can be done by using either a digital signal processor, or a pseudo logic device, or a micro-controller unit.

In accordance with the invention, peak energy or integrated peak value variation is used to determine defects.

Figure 5:
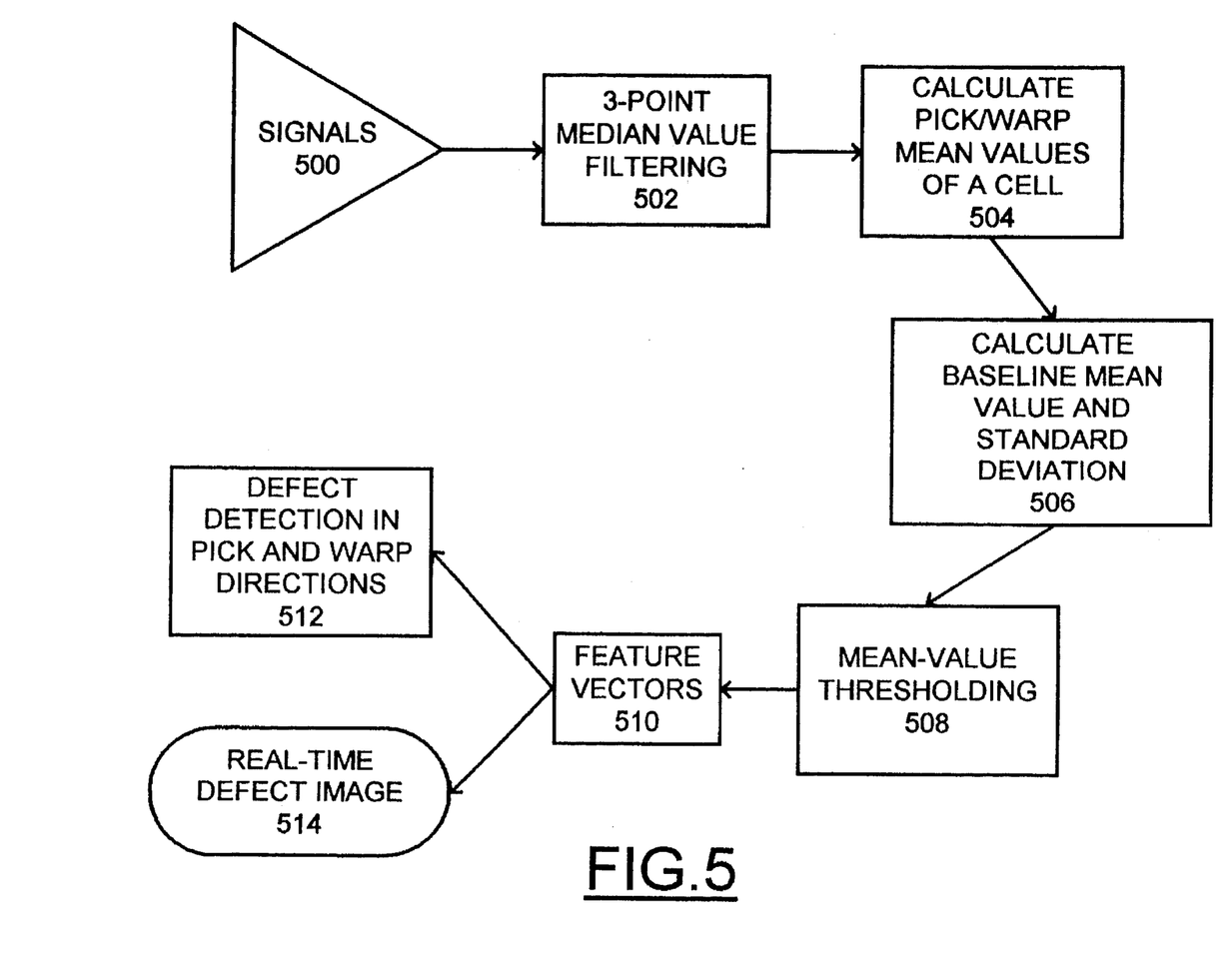
FIGS. 5 and 6 together provide a flow chart illustrating sequential steps for processing signals generated by the signal processing circuitry of FIG. 4.
Figure 6:
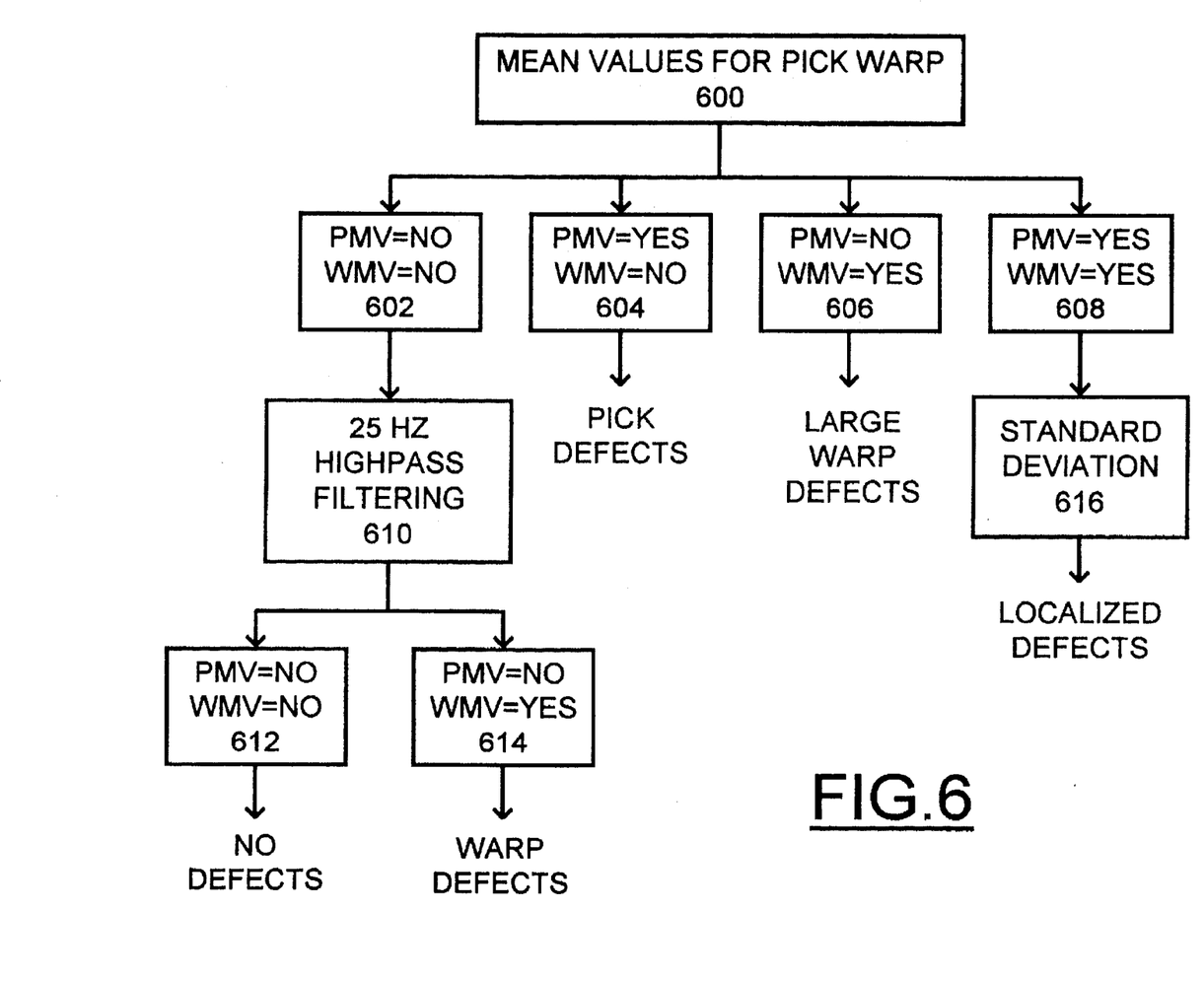

Having reference to FIGS. 5 and 6, sequential steps of the method of the invention for defect detection performed by DSP 90 are illustrated. Referring initially to FIG. 5, first DSP 90 receives the peak energy signals as indicated at a block 500. Then the peak energy signals are smoothed by using 3-point median value filtering as indicated at block 502. The purpose of the median value filtering step at block 502 is to filter out high-frequency noise, specifically in the present case, to eliminate electrical noise that may be picked up from loom operation and detection electronics. The filtering is done by simply taking the middle value (not the average value) of a number of consecutive data points (typically three data points are used) and discarding the rest.

Next the mean values in both pick (across the loom) and warp (fabric moving direction) directions inside a unit cell are calculated as indicated at a block 504. In the calculation step of mean value and standard deviation of a cell at block 504, the mean value and standard deviation of the signals of each pick or warp direction within a cell are calculated. A cell is a selected scanned area that can provide sufficient numbers of data points to give a good statistic. The size of the cell therefore depends on the weaving and scanning speeds, for example, a typical size is 600×30 (600 data points in pick direction and 30 in warp direction).

After calculating the mean and the deviation of each of the pick and warp lines in the cell at block 504, a next baseline mean value and standard deviation calculation step calculates the average mean and deviation values of the cell. The baseline mean values in both directions and their standard deviations are calculated as indicated at a block 506. A mean-value threshold in each direction is determined based on the standard deviation and is used for defect detection as indicated at a block 508. The mean-value thresholding step sets up the mean-value and standard-deviation thresholds for defect detection. The setting varies for different types of defects and fabrics, but typically 20% above or below the baseline values are chosen. Next feature vectors are generated based on the selected mean-value and standard-deviation thresholds and calculated mean value and standard deviation as indicated at a block 510. Next defect detection in both the pick and warp directions is provided based on the chosen thresholds as indicated at a block 512. A real-time defect image is generated as indicated at a block 514.

Referring now to FIG. 6, the defect detection method of the invention is illustrated, where PMV and WMV represent pick mean value and warp mean value, respectively. This method leads to about 90% detection of all the major defects. The means values for pick and warp are identified and compared with chosen threshold values at a block 600. When both the pick mean value (PMV) and warp mean value (WMV) are less than the chosen threshold values, defects are not immediately identified as indicated at a block 602 labeled PMV=NO WMV=NO. When the pick mean value (PMV) is greater than the chosen threshold value and the warp mean value (WMV) is less than the chosen threshold value, then pick defects are identified as indicated at a block 604 labeled PMV=YES WMV=NO. When the warp mean value (WMV) is greater than the chosen threshold value and the pick mean value (PMV) is less than the chosen threshold value, then warp defects are identified as indicated at a block 606 labeled PMV=NO WMV=YES. When both the pick mean value (PMV) and warp mean value (WMV) are greater than or equal to the chosen threshold values, is indicated at a block 608 labeled PMV=YES WMV=YES. When both the pick mean value (PMV) and warp mean value (WMV) are less than the chosen threshold values at block 602, then a filtering step, such as 25 Hz highpass filtering is performed as indicated at a block 610. After the highpass filtering, when both the pick mean value (PMV) and warp mean value (WMV) are less than the chosen threshold values at block 612 labeled PMV=NO WMV=NO, then no defects are identified. Otherwise, After the highpass filtering, when the warp mean value (WMV) is greater than the chosen threshold value and the pick mean value (PMV) is less than the chosen threshold value, then warp defects are identified as indicated at a block 614 labeled PMV=NO WMV=YES. When both the pick mean value (PMV) and warp mean value (WMV) are greater than or equal to the chosen threshold values at block 608, then a standard deviation comparison is provided as indicated at a block 616 to identify localized defects.

Obviously, many modifications and variations of the present invention are possible in light of the above teachings. Thus, it is to be understood that, within the scope of the appended claims, the invention may be practiced otherwise than as specifically described above.

What is claimed and desired to be secured by Letters Patent of the United States is:

1. An ultrasonic system for monitoring a fabric to identify a defect comprising:

transmitter means for generating ultrasonic waves relative to the fabric; said transmitter means including a plurality of ultrasonic transducers;

receiver means responsive to said transmitter means for receiving ultrasonic waves coupled through the fabric and generating a signal;

digital signal processing means responsive to said receiver means for processing said generated signal to identify the defect; said digital signal processing means including digitizer means for digitizing said generated signal;

median value filtering means for median value filtering said digitized signal to filter out high frequency noise; and means for calculating a mean value and standard deviation of said median value filtered signal.

2. An ultrasonic system for monitoring a fabric as recited in claim 1 wherein said transmitter means and said receiver means are spaced apart on opposite sides of the fabric and are spaced apart from the fabric, whereby said generated and received ultrasonic waves are air-coupled through the fabric.

3. An ultrasonic system for monitoring a fabric as recited in claim 1 wherein said transmitter means includes a gated sine wave generator coupled to an ultrasonic pulser for generating a pulsed ultrasonic signal and a plurality of ultrasonic transducers for transmitting ultrasonic waves through the fabric.

4. An ultrasonic system for monitoring a fabric as recited in claim 3 further includes an electrical coil coupled between said ultrasonic pulser and said plurality of ultrasonic transducers for impedance matching.

5. An ultrasonic system for monitoring a fabric as recited in claim 1 wherein said receiver means includes an ultrasonic transducer for receiving ultrasonic waves coupled through the fabric and generating a signal; preamplifier means coupled to said ultrasonic transducer means for amplifying said generated signal; and switched integrator means for generating a peak energy signal.

6. An ultrasonic system for monitoring a fabric as recited in claim 5 further includes an electrical coil coupled between said ultrasonic transducer and said preamplifier means for impedance matching.

7. An ultrasonic system for monitoring a fabric as recited in claim 6 further includes filter means coupled between said ultrasonic transducer and said preamplifier means.

8. A method for monitoring a fabric using an array of pairs of air-coupled ultrasonic transducers spaced apart from the fabric comprising the steps of:

generating ultrasonic waves relative to the fabric using a plurality of ultrasonic transducers;

receiving ultrasonic waves coupled through the fabric and generating a signal; and integrating said generated signal to identify a peak energy signal;

utilizing a computer digital signal processor to perform the steps of:

digitizing said peak energy signal;

median value filtering said digitized signal to filter out high frequency noise;

calculating a mean value and standard deviation of said median value filtered signal;

identifying mean value thresholds; and utilizing said calculated mean value and standard deviation and said identified mean value thresholds to detect a defect in the fabric.

9. A method for monitoring a fabric as recited in claim 8 further includes the step of utilizing said calculated mean value and standard deviation and said identified mean value thresholds and generating feature vectors and generating a real-time defect image.

10. A method for monitoring a fabric as recited in claim 8 includes the steps of detecting fabric defects and storing a database of fabric defect data.

* * * * *